United States Patent
Fukuhara et al.

(10) Patent No.: US 8,648,153 B2
(45) Date of Patent: Feb. 11, 2014

(54) ORGANOPOLYSILOXANE

(75) Inventors: Kazuhisa Fukuhara, Sumida-ku (JP);
Kiyotake Tada, Sumida-ku (JP);
Takashi Kodate, Wakayama (JP);
Shuichiro Kobaru, Wakayama (JP);
Noriko Tejima, Wakayama (JP)

(73) Assignee: KAO Corporation, Tokyo (JP)

( * ) Notice: Subject to any disclaimer, the term of this patent is extended or adjusted under 35 U.S.C. 154(b) by 14 days.

(21) Appl. No.: 13/504,140

(22) PCT Filed: Nov. 8, 2010

(86) PCT No.: PCT/JP2010/069818
§ 371 (c)(1),
(2), (4) Date: Apr. 26, 2012

(87) PCT Pub. No.: WO2011/062077
PCT Pub. Date: May 26, 2011

(65) Prior Publication Data
US 2012/0220723 A1 Aug. 30, 2012

(30) Foreign Application Priority Data

Nov. 18, 2009 (JP) ................................. 2009-263402

(51) Int. Cl.
| C08G 77/452 | (2006.01) |
| C08G 77/455 | (2006.01) |
| C08G 77/388 | (2006.01) |
| C08F 283/12 | (2006.01) |
| C08L 83/10  | (2006.01) |

(52) U.S. Cl.
USPC ............................................. 525/474

(58) Field of Classification Search
USPC ............................................. 525/474
See application file for complete search history.

(56) References Cited

U.S. PATENT DOCUMENTS

| 5,171,821 | A * | 12/1992 | Nozawa et al. ............... 528/125 |
| 5,618,525 | A   | 4/1997  | Bunning |
| 5,690,129 | A   | 11/1997 | Bunning |
| 5,747,016 | A   | 5/1998  | Yui et al. |
| 5,882,518 | A   | 3/1999  | Yagi et al. |
| 6,610,278 | B2* | 8/2003  | Kashimoto ................... 424/64 |
| 7,001,864 | B2* | 2/2006  | Kiso et al. ................... 502/155 |
| 2010/0203002 | A1 | 8/2010 | Fukuhara et al. |
| 2012/0216823 | A1* | 8/2012 | Fukuhara et al. ............. 132/203 |

FOREIGN PATENT DOCUMENTS

| DE | 102 05 529 A1 | 8/2003 |
| EP | 0 640 643 A2  | 3/1995 |
| EP | 0 640 643 A3  | 3/1995 |
| JP | 2 276824      | 11/1990 |
| JP | 3 287509      | 12/1991 |
| JP | 5 112423      | 5/1993 |
| JP | 7 133352      | 5/1995 |
| JP | 7 173395      | 7/1995 |
| JP | 8 40839       | 2/1996 |
| JP | 10-306163     | 11/1998 |
| JP | 10 306168     | 11/1998 |
| JP | 2002 53440    | 2/2002 |
| JP | 2004 83691    | 3/2004 |
| JP | 2008-143821   | 6/2008 |
| JP | 2009 40699    | 2/2009 |
| JP | 2009 149597   | 7/2009 |
| JP | 2009 256367   | 11/2009 |
| JP | 2010 105955   | 5/2010 |
| WO | 2009 014237   | 1/2009 |

OTHER PUBLICATIONS

International Search Report Issued Feb. 22, 2011 in PCT/JP10/69818 Filed Nov. 8, 2010.
Extended Search Report issued Jun. 11, 2013 in European Patent Application No. 10831472.5.
U.S. Appl. No. 13/505,355, filed May 1, 2012, Fukuhara, et al.
U.S. Appl. No. 13/639,313, filed Oct. 4, 2012, Kodate.

* cited by examiner

Primary Examiner — Mike M Dollinger
(74) Attorney, Agent, or Firm — Oblon, Spivak, McClelland, Maier & Neustadt, L.L.P.

(57) ABSTRACT

The present invention provides an organopolysiloxane obtained by binding, to at least two silicon atoms of an organopolysiloxane segment constituting a main chain, a poly(N-acylalkyleneimine) segment composed of a repeating unit represented by the following formula (1):

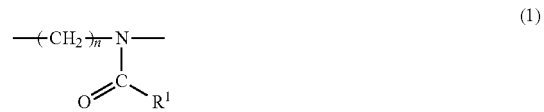

wherein $R^1$ represents a hydrogen atom or an alkyl group having from 1 to 3 carbon atoms and n is 2 or 3, via an alkylene group containing a hetero atom, wherein the poly (N-acylalkyleneimine) segment has a number-average molecular weight of from 1,600 to 3,500; a mass ratio (a/b) of the organopolysiloxane segment (a) constituting the main chain to the poly(N-acylalkyleneimine) segment (b) (which will hereinafter be called "mass ratio (a/b)", simply) is from 42/58 to 58/42; the organopolysiloxane segment between two poly(N-acylalkyleneimine) segments adjacent to each other has a weight-average molecular weight of from 1,600 to 3,500; and the organopolysiloxane segment constituting the main chain has a weight-average molecular weight of 7,000 to 100,000.

13 Claims, No Drawings

ORGANOPOLYSILOXANE

CROSS REFERENCES TO RELATED APPLICATIONS

This application is a 371 of International Patent Application No. PCT/JP10/069818, filed on Nov. 8, 2010, and claims priority to Japanese Patent Application No. 2009-263402, filed on Nov. 18, 2009.

FIELD OF THE INVENTION

The present invention relates to an organopolysiloxane having a specific structure.

BACKGROUND OF THE INVENTION

Since organopolysiloxanes have many excellent characteristics, organopolysiloxanes in various forms have been used frequently as a feel improver or a film-forming resin. For example, Patent Document 1 discloses a poly(N-acylalkyleneimine)-modified organopolysiloxane having a high elastic modulus and undergoing neither rupture nor plastic deformation within a range of a certain extensibility. According to this document, this organopolysiloxane is excellent in, for example, hair setting performance and retention property of the hair thus set, compared with conventional film-forming resins.

PRIOR ART DOCUMENT

Patent Document

[Patent Document 1] JP-A 07-133352

SUMMARY OF THE INVENTION

The present invention provides an organopolysiloxane obtained by binding, to at least two silicon atoms of an organopolysiloxane segment constituting a main chain, a poly(N-acylalkyleneimine) segment composed of a repeating unit represented by the following formula (1):

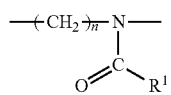
(1)

wherein $R^1$ represents a hydrogen atom or an alkyl group having from 1 to 3 carbon atoms and n stands for 2 or 3, via an alkylene group containing a hetero atom, wherein the poly (N-acylalkyleneimine) segment has a number-average molecular weight of from 1,600 to 3,500; a mass ratio (a/b) of the organopolysiloxane segment (a) constituting the main chain to the poly(N-acylalkyleneimine) segment (b) (hereinafter be called "mass ratio (a/b)", simply) is from 42/58 to 58/42; the organopolysiloxane segment between two poly(N-acylalkyleneimine) segments adjacent to each other has a weight-average molecular weight of from 1,600 to 3,500; and the organopolysiloxane segment constituting the main chain has a weight-average molecular weight of from 7,000 to 100,000.

DETAILED DESCRIPTION OF THE INVENTION

When the organopolysiloxane disclosed in Patent Document 1 is used, for example, in a hair setting agent, the resulting hair setting agent is excellent in setting performance because it has a high elastic modulus. In the meantime, this organopolysiloxane is not great in the deformation amount within which deformation occurs without causing rupture or plastic deformation, so that large deformation of the hair due to external factors (finger combing, wind, oscillation or the like) may result in rupture or deformation of a film formed on the hair. Thus, it does not exhibit sufficient performance from the standpoint of holding a hair style for long hours.

The present inventors have carried out an extensive investigation and found that an organopolysiloxane having a specific structure has a high elastic modulus and is great in the deformation amount within which deformation occurs without causing a rupture or plastic deformation, so that it has excellent properties as an elastomer.

The present invention provides an organopolysiloxane with a high elastic modulus as well as a great deformation amount (hereinafter, be called "deformable amount") within which deformation occurs without causing rupture or plastic deformation.

[Organopolysiloxane]

The organopolysiloxane of the present invention is a polymer obtained by binding the poly(N-acylalkyleneimine) segment composed of a repeating unit represented by the above formula (1) to at least two silicon atoms of the organopolysiloxane segment constituting the main chain via an alkylene group containing a hetero atom.

At least two poly(N-acylalkyleneimine) segments are bound to any of the silicon atoms constituting the organopolysiloxane segment via an alkylene group containing a hetero atom. It is preferred that they are bound to one or more silicon atoms of the organopolysiloxane segment except for those at both ends thereof via the alkylene group and more preferred that they are bound to two or more silicon atoms of the organopolysiloxane segment except for those at both ends thereof via the alkylene group. This means that the organopolysiloxane of the present invention is a graft polymer having, as a side chain thereof, at least two poly(N-acylalkyleneimine) segments each composed of a repeating unit represented by the above formula (1).

The alkylene group containing a hetero atom functions as a linking group for the poly(N-acylalkyleneimine) segment. Examples of such an alkylene group include alkylene groups having from 2 to 20 carbon atoms and containing from 1 to 3 nitrogen atoms, oxygen atoms, or sulfur atoms. Among them, groups represented by any of the following formulas (i) to (vii) are preferred, of which those represented by the formula (i) or (ii) are more preferred and those represented by the formula (i) are more preferred. In the formula, An represents a counterion of a quaternary ammonium salt and examples thereof include ethyl sulfate ion, methyl sulfate ion, chloride ion, iodide ion, sulfate ion, p-toluenesulfonate ion, and perchlorate ion.

(i)

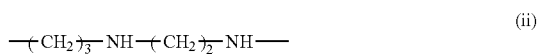
(ii)

(iii)

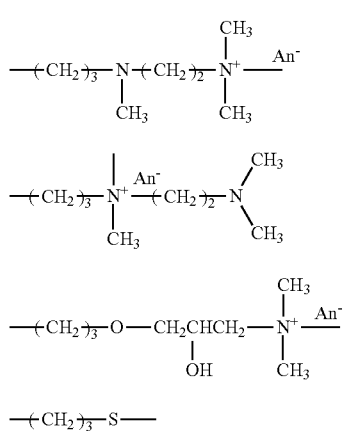

In the N-acylalkyleneimine unit constituting the poly(N-acylalkyleneimine) segment, the alkyl group having from 1 to 3 carbon atoms represented by $R^1$ in the formula (1) is, for example, a linear alkyl group having from 1 to 3 carbon atoms or a branched alkyl group having 3 carbon atoms. Specific examples thereof include a methyl group, an ethyl group, an n-propyl group, and an isopropyl group.

In the formula (1), n is the number of 2 or 3 and is preferably 2 from the standpoint of availability of raw materials for the preparation of the organopolysiloxane of the present invention.

The organopolysiloxane of the present invention can achieve both a high elastic modulus and a large deformable amount insofar as the mass ratio (a/b) falls within a range of from 42/58 to 58/42. From this viewpoint, the mass ratio (a/b) is preferably from 45/55 to 55/45, more preferably from 47/53 to 53/47.

The term "mass ratio (a/b)" as used herein means a value determined from an integral ratio of the alkyl or phenyl group in the organopolysiloxane segment to the methylene group in the poly(N-acylalkyleneimine) segment, found by subjecting a solution, which has been obtained by dissolving 5 mass % of the organopolysiloxane of the present invention in deuterated chloroform, to nuclear magnetic resonance ($^1$H-NMR) analysis. The organopolysiloxane of the present invention having the mass ratio (a/b) within the above-described range is excellent in solubility in a polar solvent such as water and handling ease after dissolving it therein.

When in the organopolysiloxane of the present invention, the organopolysiloxane segment between two poly(N-acylalkyleneimine) segments adjacent to each other has a weight-average molecular weight (hereinafter be called "MWg", simply) within a range of from 1,600 to 3,500, the resulting organopolysiloxane can exhibit a large deformable amount. From this standpoint, MWg is more preferably from 1,800 to 3,200, even more preferably from 2,000 to 3,000.

The term "the organopolysiloxane segment between (poly(N-acylalkyleneimine) segments adjacent to each other" as used herein means, as represented by the formula (2), a segment surrounded by a broken line between two points from a linkage point (linkage point α) of a poly(N-acylalkyleneimine) segment to the organopolysiloxane segment to a linkage point (linkage point β) of a poly(N-acylalkyleneimine) segment adjacent to the above-described poly(N-acylalkyleneimine) segment and composed of one $R^2SiO$ unit, one $R^6$, and y+1 pieces of $(R^2)_2SiO$ units. The term "poly(N-acylalkyleneimine) segment" means —W—$R^7$ bound to the $R^6$.

In the above formula (2), $R^2$ independently represents an alkyl group having from 1 to 22 carbon atoms or a phenyl group, $R^6$ represents an alkylene group containing a hetero atom, —W—$R^7$ represents a poly(N-acylalkyleneimine) segment, $R^7$ represents a residue of a polymerization initiator, and y is a positive number.

MWg is a molecular weight of the segment surrounded by a broken line in the above formula (2) and it may be understood as the mass (g/mol) of the organopolysiloxane segment per mole of the poly(N-acylalkyleneimine) segment. When 100% of the functional group of a modified organopolysiloxane which is a raw material compound is substituted with a poly(N-acylalkyleneimine), the value is equal to the functional group equivalent (g/mol) of the modified organopolysiloxane.

The molecular weight of the poly(N-acylalkyleneimine) segment may be calculated from the molecular weight and polymerization degree of an N-acylalkyleneimine unit or measured using gel permeation chromatography (hereinafter be called "GPC" simply). In the present invention, the molecular weight means a number-average molecular weight in terms of polystyrene (hereinafter be called "MNox", simply) as determined by GPC measurement conducted under measurement conditions described later in Examples. When the MNox falls within a range of from 1,600 to 3,500, an organopolysiloxane exhibiting a large deformable amount can be obtained. From this standpoint, the MNox is preferably from 1,800 to 3,200, more preferably from 2,000 to 3,000, even more preferably from 2,000 to 2,500.

The MWg may be calculated from the following formula (I) by using the content (mass %) (hereinafter be called "Csi", simply) of the organopolysiloxane segment constituting the main chain.

$$MWg = Csi \times MNox/(100-Csi) \qquad (I)$$

The weight-average molecular weight (hereinafter be called "MWsi", simply) of the organopolysiloxane segment constituting the main chain is from 7,000 to 100,000. From the standpoint of solubility in a polar solvent such as water and handling ease after dissolving it therein, it is preferably from 10,000 to 80,000, more preferably form 20,000 to 60,000, more preferably from 20,000 to 50,000, even more preferably from 20,000 to 40,000. The organopolysiloxane of the present invention can be easily incorporated in various products by dissolving it in a polar solvent such as water. The organopolysiloxane segment constituting the main chain has a skeleton common to a modified organopolysiloxane which is a raw material compound, so that MWsi has a weight-average molecular weight substantially equal to that of the modified organopolysiloxane which is a raw material compound. It is to be noted that the weight-average molecular weight of the modified organopolysiloxane which is a raw material compound is measured using GPC under the measurement conditions described in Examples, and is expressed in terms of polystyrene.

The weight-average molecular weight (which may hereinafter be called "MWt", simply) of the organopolysiloxane of the present invention is preferably from 20,000 to 100,000, more preferably from 30,000 to 80,000, even more preferably from 40,000 to 80,000 from the standpoint of solubility in a polar solvent such as water and handling ease after dissolving it therein. The MWt is determined using GPC under the measurement conditions described in Examples, and is expressed in terms of polystyrene.

The organopolysiloxane of the present invention has, in addition to a high elastic modulus and a great deformable amount, characteristic thermoplasticity, meaning that when heated to a temperature range of from 50 to 220° C., it shows markedly improved plasticity and softens but while the temperature returns to the room temperature after termination of heating, it restores elasticity quickly.

[Preparation Process of Organopolysiloxane]

A preparation process of the organopolysiloxane of the present invention will next be described.

The organopolysiloxane of the present invention is prepared, for example, by reacting a modified organopolysiloxane represented by the following formula (3):

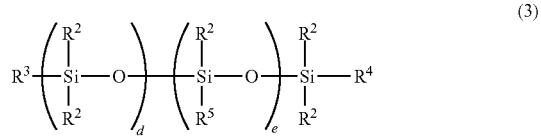

(3)

wherein $R^2$ has the same meaning as described above, $R^3$ and $R^4$ independently represents the same group as $R^2$ or a monovalent group represented by any of the following formulas (viii) to (xiii):

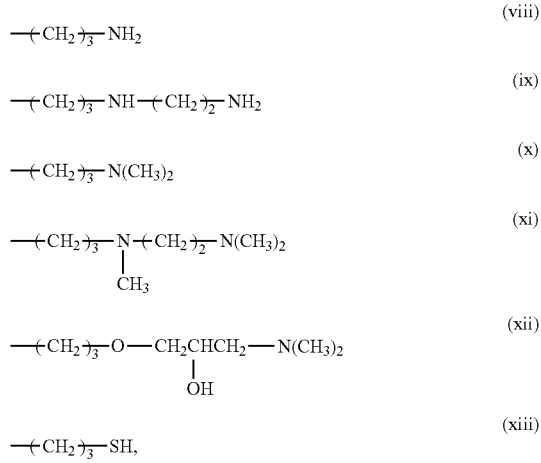

$R^5$ represents a monovalent group represented by any of the above formulas (viii) to (xiii), d represents the number from 91.5 to 1255.0, and e represents the number from 2.0 to 62.5, with a terminal-reactive poly(N-acylalkyleneimine) obtainable by ring-opening polymerization of a cyclic imino ether represented by the following formula (4):

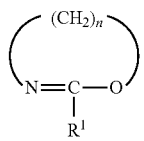

(4)

wherein $R^1$ and n have the same meanings as described above.

In the ring-opening polymerization of the cyclic imino ether represented by the formula (4) (hereinafter be called "cyclic imino ether (4)", simply), a polymerization initiator may be used. As the polymerization initiator, compounds having high electrophilic reactivity, for example, alkyl esters of a strong acid may be used. Examples thereof include alkyl ester benzenesulfonates, alkyl ester p-toluenesulfonates, alkyl ester trifluoromethanesulfonates, alkyl ester trifluoroacetates, and dialkyl ester sulfates. Of these, dialkyl ester sulfates are preferred.

Examples of a solvent for polymerization include acetic acid esters such as ethyl acetate and propyl acetate, ethers such as diethyl ether, diisopropyl ether, dioxane, and tetrahydrofuran, ketones such as acetone and methyl ethyl ketone, halogen solvents such as chloroform and methylene chloride, nitrile-based solvents such as acetonitrile and benzonitrile, and aprotic polar solvents such as N,N-dimethylformamide, N,N-dimethylacetamide, and dimethylsulfoxide. Of these, acetic acid esters are preferred. The used amount of the solvent is usually from 20 to 2,000 parts by mass based on 100 parts by mass of the cyclic imino ether (4).

The polymerization temperature is typically from 30 to 170° C., preferably from 40 to 150° C. The polymerization time varies depending on the polymerization temperature or the like and it is typically from 1 to 60 hours.

Using, for example, 2-substituted-2-oxazoline as the cyclic imino ether (4) obtains poly(N-acylethyleneimine) which is a compound of the above formula (1) having 2 as n, while using 2-substituted-dihydro-2-oxazine obtains poly(N-acylpropyleneimine) which is a compound of the above formula (1) having 3 as n.

The poly(N-acylalkyleneimine) obtainable by the living polymerization of the cyclic imino ether (4) has, at the end thereof, a reactive group. Therefore, the organopolysiloxane of the present invention can be obtained by reacting the reactive group at the end of the poly(N-acylalkyleneimine) with the reactive group represented by any of the above formulas (viii) to (xiii) which the modified organopolysiloxane represented by the formula (3) has.

The preparation process using living polymerization is effective in that it is possible to easily control the polymerization degree with used amounts of the cyclic imino ether (4) and the polymerization initiator as shown below in theoretical formula (II) and in addition, it is possible to obtain a substantially monodisperse poly(N-acylalkyleneimine) having a molecular weight distribution narrower than that obtainable by the typical radical polymerization.

$$MNi = \frac{\text{The number of moles of } cyclicimino \text{ ether (4)}}{\text{The number of moles of polymerization initator}} \times \text{Molecular weight of } cyclicimino \text{ ether (4)} + \text{Molecular weight of polymerization initiator} \quad (II)$$

[MNi: calculated number-average molecular weight of poly(N-acylalkyleneimine) obtainable by living polymerization]

The used amount of the cyclic imino ether (4) and the used amount of the polymerization initiator are preferably those giving the MNi in the formula (II) of from 1,600 to 3,500, more preferably from 1,800 to 3,200, even more preferably from 2,000 to 3,000.

The weight-average molecular weight of the modified organopolysiloxane represented by the formula (3) is preferably from 7,000 to 100,000, more preferably from 10,000 to 80,000, more preferably from 20,000 to 60,000, more preferably from 20,000 to 50,000, even more preferably from 20,000 to 40,000 from the standpoint of solubility of the organopolysiloxane thus obtained in a polar solvent such as water and handling ease after dissolving it therein.

Also, the functional group equivalent of the modified organopolysiloxane represented by the formula (3) has an upper limit in order to satisfy both the mass ratio (a/b) and MWg of the organopolysiloxane of the present invention. From this viewpoint and a viewpoint of providing the main chain with adequate hydrophobicity, the functional group equivalent is preferably from 500 to 3,500, more preferably from 800 to 3,200, and even more preferably from 1,000 to 3,000. The term "functional group equivalent of the modified organopolysiloxane represented by the formula (3)" means a value obtained by dividing the weight-average molecular weight of the modified organopolysiloxane represented by the formula (3) by an average of the number of $R^5$ per molecule of the modified organopolysiloxane.

The modified organopolysiloxane represented by the formula (3) and the terminal-reactive poly(N-acylalkyleneimine) are used in amounts to give the mass ratio of them (modified organopolysiloxane/terminal-reactive poly(N-acylalkyleneimine)) within a range of preferably from 42/58 to 58/42, more preferably from 45/55 to 55/45, even more preferably from 47/53 to 53/47 from the standpoint of the elastic modulus and deformable amount of the organopolysiloxane thus obtained.

EXAMPLES

The present invention will hereinafter be described specifically based on Examples. The present invention should not be limited to or by these Examples. In the synthesis of each organopolysiloxane, various molecular weights were measured under the following measurement conditions.

<Measurement Conditions of Weight-Average Molecular Weight of Modified Organopolysiloxane>
 Column: Super HZ4000+Super HZ2000 (product of Tosoh Corporation)
 Eluent: 1 mM triethylamine/THF
 Flow rate: 0.35 mL/min
 Column temperature: 40° C.
 Detector: UV
 Sample: 50 µL <Measurement Conditions of MNox and MWt>
 Column: K-804L (product of Tosoh Corporation). Two columns connected in series.
 Eluent: 1 mM dimethyldodecylamine/chloroform
 Flow rate: 1.0 mL/min
 Column temperature: 40° C.
 Detector: RI
 Sample: 50 µL The $^1$H-NMR measurement for determining the mass ratio (a/b) was conducted under the following conditions.

<$^1$H-NMR Measurement Conditions>
The composition of the polymer thus obtained was confirmed by $^1$H-NMR (400 MHz, product of Varian, Inc.).

A solution obtained by dissolving 0.5 g of a sample in 2 g of a solvent for measurement (deuterated chloroform) was measured.

PULSE SEQUENCE
 Relax. delay: 30 seconds. Pulse: 45 degrees.
 Cumulated number: 8 times.
 Peaks confirmed: peak near 0 ppm: methyl group of polydimethylsiloxane, peak near 3.4 ppm: methylene portion of ethylene imine.

A silicone/poly(N-propionylethyleneimine) ratio was determined from each integral value.

Example 1

Synthesis of Organopolysiloxane A

A terminal-reactive poly(N-propionylethyleneimine) was synthesized by dissolving 6.17 g (0.04 mol) of diethyl sulfate and 93.8 g (0.947 mol) of 2-ethyl-2-oxazoline in 203 g of dehydrated ethyl acetate and heating the resulting solution under reflux for 8 hours in a nitrogen atmosphere. It had MNox of 2,500 as measured by GPC. A 33% ethyl acetate solution of 100 g of side-chain primary aminopropyl-modified polydimethylsiloxane (weight-average molecular weight: 26,000, amine equivalent (functional group equivalent): 2,000) was added thereto at a time and the resulting mixture was heated under reflux for 10 hours. The solvent was removed from the reaction mixture under reduced pressure to obtain organopolysiloxane A as a pale yellow solid. The resulting product had a mass ratio (a/b) of 50/50 and MWt of 56,000. Neutralizing titration with hydrochloric acid while using methanol as a solvent revealed that about 20 mole % of amino groups remained.

Example 2

Synthesis of Organopolysiloxane B

A terminal-reactive poly(N-propionylethyleneimine) was synthesized by dissolving 6.18 g (0.04 mol) of diethyl sulfate and 75.6 g (0.762 mol) of 2-ethyl-2-oxazoline in 166 g of dehydrated ethyl acetate and heating the resulting solution under reflux for 8 hours in a nitrogen atmosphere. It had MNox of 2,040 as measured by GPC. A 33% ethyl acetate solution of 100 g of side-chain primary aminopropyl-modified polydimethylsiloxane (weight-average molecular weight: 46,000, amine equivalent (functional group equivalent): 1,870) was added thereto at a time and the resulting mixture was heated under reflux for 10 hours. The solvent was removed from the reaction mixture under reduced pressure to obtain organopolysiloxane B as a pale yellow solid. It had a mass ratio (a/b) of 55/45 and MWt of 74,000. Neutralizing titration with hydrochloric acid while using methanol as a solvent revealed that about 25 mole % of amino groups remained.

Example 3

Synthesis of Organopolysiloxane C

A terminal-reactive poly(N-propionylethyleneimine) was synthesized by dissolving 7.22 g (0.05 mol) of diethyl sulfate and 110.2 g (1.11 mol) of 2-ethyl-2-oxazoline in 238 g of dehydrated ethyl acetate and heating the resulting solution under reflux for 8 hours in a nitrogen atmosphere. It had MNox of 2,500 as measured by GPC. A 33% ethyl acetate solution of 100 g of side-chain primary aminopropyl-modified polydimethylsiloxane (weight-average molecular weight: 26,000, amine equivalent (functional group equivalent): 2,000) was added thereto at a time and the resulting mixture was heated under reflux for 10 hours. The solvent was removed from the reaction mixture under reduced pressure to obtain organopolysiloxane C as a pale yellow solid. It had a mass ratio (a/b) of 46/54 and MWt of 44,000. Neutralizing titration with hydrochloric acid while using methanol as a solvent revealed that about 4 mole % of amino groups remained.

Example 4

Synthesis of Organopolysiloxane D

A terminal-reactive poly(N-propionylethyleneimine) was synthesized by dissolving 6.10 g (0.04 mol) of diethyl sulfate and 93.9 g (0.95 mol) of 2-ethyl-2-oxazoline in 203 g of dehydrated ethyl acetate and heating the resulting solution under reflux for 8 hours in a nitrogen atmosphere. It had MNox of 2,530 as measured by GPC. A 33% ethyl acetate solution of 100 g of side-chain primary aminopropyl-modified polydimethylsiloxane (weight-average molecular weight: 46,000, amine equivalent (functional group equivalent): 1,870) was added thereto at a time and the resulting mixture was heated under reflux for 10 hours. The solvent was removed from the reaction mixture under reduced pressure to obtain organopolysiloxane D as a pale yellow solid. It had a mass ratio (a/b) of 50/50 and MWt of 53,000. Neutralizing titration with hydrochloric acid while using methanol as a solvent revealed that about 26 mole % of amino groups remained.

Comparative Example 1

Synthesis of Organopolysiloxane E

A terminal-reactive poly(N-propionylethyleneimine) was synthesized by dissolving 3.84 g (0.02 mol) of diethyl sulfate and 96.2 g (0.97 mol) of 2-ethyl-2-oxazoline in 203 g of dehydrated ethyl acetate and heating the resulting solution under reflux for 8 hours in a nitrogen atmosphere. It had MNox of 4,000 as measured by GPC. A 33% ethyl acetate solution of 100 g of side-chain primary aminopropyl-modified polydimethylsiloxane (weight-average molecular weight: 26,000, amine equivalent (functional group equivalent): 2,000) was added thereto at a time and the resulting mixture was heated under reflux for 10 hours. The solvent was removed from the reaction mixture under reduced pressure to obtain organopolysiloxane E as a pale yellow solid. It had a mass ratio (a/b) of 50/50 and MWt of 100,000. Neutralizing titration with hydrochloric acid while using methanol as a solvent revealed that about 49 mole % of amino groups remained.

Comparative Example 2

Synthesis of Organopolysiloxane F

A terminal-reactive poly(N-propionylethyleneimine) was synthesized by dissolving 9.10 g (0.06 mol) of diethyl sulfate and 141 g (1.42 mol) of 2-ethyl-2-oxazoline in 304 g of dehydrated ethyl acetate and heating the resulting solution under reflux for 8 hours in a nitrogen atmosphere. It had MNox of 2,540 as measured by GPC. A 33% ethyl acetate solution of 100 g of side-chain primary aminopropyl-modified polydimethylsiloxane (weight-average molecular weight: 46,000, amine equivalent (functional group equivalent):1,440) was added thereto at a time and the resulting mixture was heated under reflux for 10 hours. The solvent was removed from the reaction mixture under reduced pressure to obtain organopolysiloxane F as a pale yellow solid. It had a mass ratio (a/b) of 40/60 and MWt of 100,000. Neutralizing titration with hydrochloric acid while using methanol as a solvent revealed that about 15 mole % of amino groups remained.

Comparative Example 3

Synthesis of Organopolysiloxane G

A terminal-reactive poly(N-propionylethyleneimine) was synthesized by dissolving 11.8 g (0.08 mol) of diethyl sulfate and 88.2 g (0.89 mol) of 2-ethyl-2-oxazoline in 203 g of dehydrated ethyl acetate and heating the resulting solution under reflux for 8 hours in a nitrogen atmosphere. It had MNox of 1,310 as measured by GPC. A 33% ethyl acetate solution of 100 g of side-chain primary aminopropyl-modified polydimethylsiloxane (weight-average molecular weight: 10,000, amine equivalent (functional group equivalent): 1,090) was added thereto at a time and the resulting mixture was heated under reflux for 10 hours. The solvent was removed from the reaction mixture under reduced pressure to obtain organopolysiloxane G as a pale yellow solid. It had a mass ratio (a/b) of 50/50 and MWt of 23,000. Neutralizing titration with hydrochloric acid while using methanol as a solvent revealed that about 17 mole % of amino groups remained.

Comparative Example 4

Synthesis of Organopolysiloxane H

A terminal-reactive poly(N-propionylethyleneimine) was synthesized by dissolving 3.77 g (0.02 mol) of diethyl sulfate and 57.5 g (0.58 mol) of 2-ethyl-2-oxazoline in 124 g of dehydrated ethyl acetate and heating the resulting solution under reflux for 8 hours in a nitrogen atmosphere. It had MNox of 2,510 as measured by GPC. A 33% ethyl acetate solution of 100 g of side-chain primary aminopropyl-modified polydimethylsiloxane (weight-average molecular weight: 26,000, amine equivalent (functional group equivalent): 2,000) was added thereto at a time and the resulting mixture was heated under reflux for 10 hours. The solvent was removed from the reaction mixture under reduced pressure to obtain organopolysiloxane H as a pale yellow solid. It had a mass ratio (a/b) of 62/38 and MWt of 65,000. Neutralizing titration with hydrochloric acid while using methanol as a solvent revealed that about 50 mole % of amino groups remained.

[Evaluation]

By using the organopolysiloxanes obtained in Examples 1 to 4 and Comparative Examples 1 to 4 as a sample, their elastic modulus, extensibility, and solubility in water were measured in accordance with the following methods. The results are collectively shown in Table 1.

Samples to be used for the measurement of the elastic modulus and extensibility were prepared using the following film formation process.

<Film Formation Process>

An adequate amount of an ethanol solution of organopolysiloxane (50 wt %) was cast on a Teflon (trade name) petri dish and dried for 5 days while flowing nitrogen at room temperature. Then, it was dried under reduced pressure (40 kPa) while flowing nitrogen for 8 hours at room temperature to obtain a pale yellow transparent film of about 1 mm thick. The film thus obtained was cut into pieces and the resulting pieces were used as a sample for the measurement of an elastic modulus and extensibility.

<Measurement of Elastic Modulus>

The elastic modulus of each sample was measured in accordance with the following method. When the film has an elastic modulus of $5 \times 10^6$ Pa or more, the organopolysiloxane used as a hair setting agent has a high hair setting power.

Apparatus used for measurement: Dynamic viscoelasticity measuring apparatus "DVA-225" (product of IT Keisoku Seigyo Co., Ltd.)
  Measurement mode: Shear mode
  Strain: from 0.01 to 0.1%
  Frequency: 1 Hz
  Sample size: (0.8 to 1.5)×(8 to 10)×(5 to 6) mm
  Measured at: 25° C.

<Measurement of Extensibility>

The term "extensibility" as used herein means a ratio, relative to an initial sample length (length before stretching), of a deformation amount of a sample at rupture, which is calculated in accordance with the following equation (III) by using a sample length at rupture in a stretching direction as a result of stretching the sample under the following measurement conditions and the initial sample length. When the sample shows an extensibility of 50% or more, the film formed on the hair using the corresponding organopolysiloxane as a setting agent is not easily broken even by large hair deformation due to external factors (finger combing, wind, oscillation, or the like) and the hair style thus set can be held for long hours.

Extensibility (%)=(length of a sample at rupture in a stretching direction−initial length of the sample)/ initial length of the sample  (III)

Apparatus: Tensilon RTC (product of A&D Company)
  Measurement mode: Stretching
  Sample size: (0.8 to 1.0)×(4.0 to 6.0)×(38.0 to 40.0) mm
  Measured at: 25° C.
  Rate of stretching: 300 mm/min <Measurement of Water Solubility>

A 5 wt % aqueous solution or dispersion of each sample was prepared and the transmittance (T %) of the resulting liquid was measured in accordance with the following conditions. The transmittance of 50% or more suggests easy incorporation of the sample in water.
  Apparatus: UV-VIS spectrophotometer UV-2550 (product of Shimadzu Corporation)
  Measurement mode: transmittance
  Measurement wavelength: 660 nm
  Sample: 5 wt % dispersion in deionized water
  Optical path length: 1 cm It has been found clearly from Examples and Comparative Examples in Table 1 that the organopolysiloxanes of the present invention are excellent elastomers having a great deformable amount while having a high elastic modulus. In addition, the organopolysiloxanes of the present invention are excellent in water solubility.

The invention claimed is:

1. An organopolysiloxane obtained by binding, to at least two silicon atoms of an organopolysiloxane segment constituting a main chain, a poly(N-acylalkyleneimine) segment comprising a repeating unit represented by the following formula (1):

wherein $R^1$ represents a hydrogen atom or an alkyl group having from 1 to 3 carbon atoms and n is 2 or 3, via an alkylene group containing a hetero atom,
wherein the poly(N-acylalkyleneimine) segment has a number-average molecular weight of from 1,600 to 3,500; a mass ratio (a/b) of the organopolysiloxane segment (a) constituting the main chain to the poly(N-acylalkyleneimine) segment (b) is from 45/55 to 55/45; the organopolysiloxane segment between two poly(N-acylalkyleneimine) segments adjacent to each other has a weight-average molecular weight of from 1,600 to 3,500; and the organopolysiloxane segment constituting the main chain has a weight-average molecular weight of 7,000 to 100,000.

2. The organopolysiloxane according to claim 1, wherein, of the silicon atoms of the organopolysiloxane segment constituting the main chain, to which the poly(N-acylalkyleneimine) segment is bound via the alkylene group containing a hetero atom, one or more silicon atoms are silicon atoms other than silicon atoms at both ends of the organopolysiloxane segment.

3. The organopolysiloxane according to claim 1, wherein the alkylene group containing a hetero atom is an alkylene group having from 2 to 20 carbon atoms and containing from one to three nitrogen atoms, oxygen atoms, or sulfur atoms.

4. The organopolysiloxane according to claim 1, wherein the mass ratio (a/b) of the organopolysiloxane segment (a) constituting the main chain and the poly(N-acylalkyleneimine) segment (b) is from 47/53 to 55/45.

5. The organopolysiloxane according to claim 1, wherein n of formula (1) is 2.

TABLE 1

|  | Example 1 | Example 2 | Example 3 | Example 4 | Comp. Ex. 1 | Comp. Ex. 2 | Comp. Ex. 3 | Comp. Ex. 4 |
| --- | --- | --- | --- | --- | --- | --- | --- | --- |
| Organopolysiloxane | A | B | C | D | E | F | G | H |
| MNox | 2,500 | 2,040 | 2,500 | 2,530 | 4,000 | 2,540 | 1,310 | 2,510 |
| MWsi* | 26,000 | 46,000 | 2,6000 | 46,000 | 26,000 | 46,000 | 10,000 | 26,000 |
| MWg | 2,500 | 2,490 | 2,080 | 2,530 | 4,000 | 1,690 | 1,310 | 4,000 |
| Mass ratio (a/b) | 50/50 | 55/45 | 46/54 | 50/50 | 50/50 | 40/60 | 50/50 | 62/38 |
| Elastic modulus (Pa) | $1 \times 10^7$ | $8 \times 10^6$ | $2 \times 10^7$ | $2 \times 10^7$ | $8 \times 10^6$ | $3 \times 10^7$ | $4 \times 10^6$ | $2 \times 10^6$ |
| Extensibility (%) | 170 | 300 | 60 | 150 | 20 | 10 | 20 | 300 |
| Transmittance (T %) | 95 | 51 | 96 | 61 | 1 | 96 | 13 | —** |

*Weight-average molecular weight of side-chain primary aminopropyl-modified polydimethylsiloxane was used.
**Not measured due to precipitation.

6. The organopolysiloxane according to claim 1, wherein the poly(N-acylalkyleneimine) segment (b) has a number-average molecular weight of from 2,000 to 3,000.

7. The organopolysiloxane according to claim 1, wherein a organopolysiloxane segment between two poly(N-acylalkyleneimine) segments adjacent to each other has a weight-average molecular weight of from 2,000 to 3,000.

8. The organopolysiloxane according to claim 1, wherein the organopolysiloxane segment constituting the main chain has a weight-average molecular weight of 20,000 to 50,000.

9. The organopolysiloxane according to claim 1, wherein the organopolysiloxane segment constituting the main chain has a weight-average molecular weight of from 20,000 to 40,000.

10. The organopolysiloxane according to claim 1, wherein the organopolysiloxane has a weight-average molecular weight of from 20,000 to 100,000.

11. The organopolysiloxane according to claim 1, wherein the organopolysiloxane has a weight-average molecular weight of from 40,000 to 80,000.

12. The organopolysiloxane according to claim 2, wherein the alklyene group containing the hetero atom is a group selected from the group consisting of

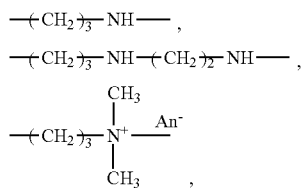

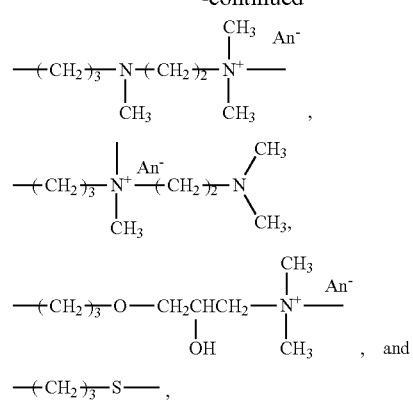

wherein An⁻ represents a counterion of a quaternary ammonium salt.

13. The organopolysiloxane according to claim 2, wherein the alklyene group containing the hetero atom is a group selected from the group consisting of —(CH₂)₃—NH—, and

—(CH₂)₃—NH—(CH₂)₂—NH—.

* * * * *